US008943168B2

(12) United States Patent
Wiesner et al.

(10) Patent No.: US 8,943,168 B2
(45) Date of Patent: *Jan. 27, 2015

(54) REMOTE MONITORING SYSTEMS FOR MONITORING MEDICAL DEVICES VIA WIRELESS COMMUNICATION NETWORKS

(71) Applicant: Covidien LP, Mansfield, MA (US)

(72) Inventors: Joel D. Wiesner, St. Peters, MO (US); Robert B. Gaines, Lake Saint Louis, MO (US); Shawn Bankert, North Attleboro, MA (US)

(73) Assignee: Covidien LP, Mansfield, MA (US)

( * ) Notice: Subject to any disclaimer, the term of this patent is extended or adjusted under 35 U.S.C. 154(b) by 60 days.

This patent is subject to a terminal disclaimer.

(21) Appl. No.: 14/154,285

(22) Filed: Jan. 14, 2014

(65) Prior Publication Data

US 2014/0152466 A1    Jun. 5, 2014

Related U.S. Application Data

(63) Continuation of application No. 13/037,886, filed on Mar. 1, 2011.

(51) Int. Cl.
*G06F 15/16* (2006.01)
*G06F 19/00* (2011.01)
(Continued)

(52) U.S. Cl.
CPC .......... *G06F 19/3418* (2013.01); *A61B 5/0026* (2013.01); *H04L 49/25* (2013.01); *H04L 45/70* (2013.01)
USPC ........................................................ 709/217

(58) Field of Classification Search
CPC . A61B 5/0026; G06F 19/3418; H04L 49/006; H04L 45/00; H04L 67/00
USPC ........................................................ 709/217
See application file for complete search history.

(56) References Cited

U.S. PATENT DOCUMENTS 5,451,839 A    9/1995  Rappaport et al.
5,936,539 A    8/1999  Fuchs
(Continued)

FOREIGN PATENT DOCUMENTS

EP    2 227 063         9/2010
KR    10-2008-0016458   2/2008
(Continued)

OTHER PUBLICATIONS

Response filed Feb. 18, 2014 for Office Action dated Sep. 27, 2013 for U.S. Appl. No. 13/241,620; 24 pages.
(Continued)

*Primary Examiner* — Adnan Mirza
(74) *Attorney, Agent, or Firm* — Lisa E. Winsor, Esq.

(57) ABSTRACT

A remote monitoring system for monitoring a plurality of medical devices at a patient care or home care facility. The system includes a device integration server in communication with wireless relay modules for receiving data packets from the medical devices including an identifier and data for each medical device. The system also includes a data management system and an outbound web server. The data management system is configured to log data for the medical devices. The web server is configured to provide webpages including the data of the medical devices for display on a remote monitoring computer, subject to authentication of an associated data request from the monitoring computer. The Web server is configurable to look up patient information from a secure source when user has appropriate permissions. In addition, the device integration server is configured to process alert messages received from the wireless relay modules and, in response, to transmit text message information to the wireless relay modules to be relayed to one or more text messaging recipients.

24 Claims, 11 Drawing Sheets

(51) Int. Cl.
*A61B 5/00* (2006.01)
*H04L 12/947* (2013.01)
*H04L 12/721* (2013.01)

(56) References Cited

U.S. PATENT DOCUMENTS

| | | |
|---|---|---|
| 6,221,012 B1 | 4/2001 | Maschke et al. |
| 6,377,162 B1 | 4/2002 | Delestienne et al. |
| 6,377,806 B1 | 4/2002 | Tokuyoshi |
| 6,442,433 B1 | 8/2002 | Linberg |
| 6,519,569 B1 | 2/2003 | White et al. |
| 6,578,002 B1 | 6/2003 | Derzay et al. |
| 6,790,198 B1 | 9/2004 | White et al. |
| 6,839,753 B2 | 1/2005 | Biondi et al. |
| 7,028,182 B1 | 4/2006 | Killcommons |
| 7,050,984 B1 | 5/2006 | Kerpelman et al. |
| 7,082,460 B2 | 7/2006 | Hansen et al. |
| 7,178,149 B2 | 2/2007 | Hansen |
| 7,185,014 B1 | 2/2007 | Hansen |
| 7,236,936 B2 | 6/2007 | White et al. |
| 7,294,105 B1 | 11/2007 | Islam |
| 7,316,648 B2 | 1/2008 | Kelly |
| 7,349,947 B1 | 3/2008 | Slage et al. |
| 7,508,787 B2 | 3/2009 | Doshi et al. |
| 7,529,561 B2 | 5/2009 | Heinonen et al. |
| 7,539,532 B2 | 5/2009 | Tran |
| 7,539,533 B2 | 5/2009 | Tran |
| 7,558,622 B2 | 7/2009 | Tran |
| 7,613,169 B2 | 11/2009 | Vaittinen et al. |
| 7,645,258 B2 | 1/2010 | White et al. |
| 7,707,047 B2 | 4/2010 | Hasan et al. |
| 7,733,224 B2 | 6/2010 | Tran |
| 7,749,164 B2 | 7/2010 | Davis |
| 7,752,058 B2 | 7/2010 | Sasaki et al. |
| 7,827,040 B2 | 11/2010 | Brown |
| 7,873,772 B2 | 1/2011 | Waldhoff et al. |
| 7,937,370 B2 | 5/2011 | Hansen |
| 7,949,164 B2 | 5/2011 | Degani et al. |
| 7,949,404 B2 | 5/2011 | Hill |
| 7,978,062 B2 | 7/2011 | LaLonde et al. |
| 8,002,701 B2 | 8/2011 | John et al. |
| RE42,934 E | 11/2011 | Thompson |
| 8,073,008 B2 | 12/2011 | Mehta et al. |
| 8,108,543 B2 | 1/2012 | Hansen |
| 8,125,318 B2 | 2/2012 | Heimbrock et al. |
| 8,326,648 B2 | 12/2012 | Kenedy et al. |
| 8,428,722 B2 | 4/2013 | Verhoef et al. |
| 2002/0178126 A1 | 11/2002 | Beck et al. |
| 2002/0198473 A1 | 12/2002 | Kumar et al. |
| 2004/0155772 A1 | 8/2004 | Medema et al. |
| 2004/0204743 A1 | 10/2004 | McGrath et al. |
| 2005/0010093 A1 | 1/2005 | Ford et al. |
| 2005/0201300 A1 | 9/2005 | Bridgelall |
| 2005/0243988 A1 | 11/2005 | Barclay et al. |
| 2005/0288571 A1 | 12/2005 | Perkins et al. |
| 2006/0154642 A1 | 7/2006 | Scannell, Jr. |
| 2006/0238333 A1 | 10/2006 | Welch et al. |
| 2007/0106126 A1 | 5/2007 | Mannheimer et al. |
| 2007/0156033 A1 | 7/2007 | Causey, III et al. |
| 2007/0180140 A1 | 8/2007 | Welch et al. |
| 2007/0216764 A1 | 9/2007 | Kwak |
| 2007/0254593 A1 | 11/2007 | Jollota et al. |
| 2007/0258395 A1 | 11/2007 | Jollota et al. |
| 2007/0272670 A1 | 11/2007 | Chen |
| 2007/0276270 A1 | 11/2007 | Tran |
| 2008/0004907 A1 | 1/2008 | Bayne |
| 2008/0012761 A1 | 1/2008 | Derrick et al. |
| 2008/0071234 A1 | 3/2008 | Kelch et al. |
| 2008/0108880 A1 | 5/2008 | Young et al. |
| 2008/0281168 A1 | 11/2008 | Gibson et al. |
| 2009/0023391 A1 | 1/2009 | Falck |
| 2009/0058635 A1 | 3/2009 | LaLonde et al. |
| 2009/0105549 A1 | 4/2009 | Smith et al. |
| 2009/0128320 A1 | 5/2009 | Needham et al. |
| 2009/0184835 A1 | 7/2009 | Deaver, Sr. et al. |
| 2009/0203329 A1 | 8/2009 | White et al. |
| 2009/0247114 A1 | 10/2009 | Sennett et al. |
| 2009/0252117 A1 | 10/2009 | Sherman et al. |
| 2009/0299788 A1 | 12/2009 | Huber et al. |
| 2010/0027518 A1 | 2/2010 | Wang |
| 2010/0077115 A1 | 3/2010 | Rofougran |
| 2010/0079276 A1 | 4/2010 | Collins et al. |
| 2010/0080200 A1 | 4/2010 | Stewart |
| 2010/0085948 A1 | 4/2010 | Yu et al. |
| 2010/0117835 A1 | 5/2010 | Nanikashvili |
| 2010/0138235 A1 | 6/2010 | Marks et al. |
| 2010/0166170 A1 | 7/2010 | East et al. |
| 2010/0198142 A1 | 8/2010 | Sloan et al. |
| 2010/0217723 A1 | 8/2010 | Sauerwein, Jr. et al. |
| 2010/0219250 A1 | 9/2010 | Wang |
| 2010/0234695 A1 | 9/2010 | Morris |
| 2010/0279647 A1 | 11/2010 | Jacobs et al. |
| 2010/0317286 A1 | 12/2010 | Jung et al. |
| 2010/0318578 A1 | 12/2010 | Treu et al. |
| 2011/0021902 A1 | 1/2011 | Kim et al. |
| 2011/0032822 A1 | 2/2011 | Soomro |
| 2011/0087756 A1 | 4/2011 | Biondi et al. |
| 2011/0093297 A1 | 4/2011 | Dicks et al. |
| 2011/0148624 A1 | 6/2011 | Eaton et al. |
| 2011/0161111 A1 | 6/2011 | Dicks et al. |
| 2011/0270045 A1 | 11/2011 | Lebel et al. |
| 2011/0280224 A1 | 11/2011 | Falck et al. |
| 2011/0292862 A1 | 12/2011 | Shimizu |
| 2012/0004925 A1 | 1/2012 | Braverman et al. |
| 2012/0108917 A1 | 5/2012 | Libbus et al. |
| 2012/0182143 A1 | 7/2012 | Gaines et al. |
| 2012/0182894 A1 | 7/2012 | Gaines et al. |
| 2012/0182924 A1 | 7/2012 | Gaines et al. |
| 2012/0182927 A1 | 7/2012 | Wiesner et al. |
| 2012/0184207 A1 | 7/2012 | Gaines et al. |
| 2012/0184237 A1 | 7/2012 | Gaines et al. |
| 2012/0185268 A1 | 7/2012 | Wiesner et al. |
| 2012/0226768 A1 | 9/2012 | Gaines et al. |
| 2012/0226771 A1 | 9/2012 | Harrington et al. |
| 2012/0256751 A1 | 10/2012 | Nallabelli et al. |
| 2012/0293323 A1 | 11/2012 | Kaib et al. |
| 2013/0015966 A1 | 1/2013 | Soomro et al. |
| 2013/0021169 A1 | 1/2013 | Soomro et al. |
| 2013/0022022 A1 | 1/2013 | Schmitt |
| 2013/0162426 A1 | 6/2013 | Wiesner et al. |
| 2013/0278414 A1 | 10/2013 | Sprigg et al. |
| 2014/0009271 A1 | 1/2014 | Collins et al. |

FOREIGN PATENT DOCUMENTS

| | | |
|---|---|---|
| KR | 10-2009-0122968 | 12/2009 |
| KR | 10-2010-0028318 | 3/2010 |
| KR | 10 2010 0028318 A | 5/2010 |
| WO | WO 94/16617 | 8/1994 |
| WO | WO 98/14228 | 4/1998 |
| WO | WO 03/048919 A1 | 6/2003 |
| WO | WO 2004/070994 A2 | 8/2004 |
| WO | WO 2004/070994 A3 | 8/2004 |
| WO | WO 2005/057294 A1 | 6/2005 |
| WO | WO 2005/057834 A2 | 6/2005 |
| WO | WO 2005/098736 A2 | 10/2005 |
| WO | WO 2008/052034 A1 | 5/2008 |
| WO | WO 2009/032134 A2 | 3/2009 |

OTHER PUBLICATIONS

Response filed Feb. 13, 2014 for Office Action dated Sep. 5, 2013 for U.S. Appl. No. 13/006,769; 18 pages.
Response filed with RCE on Feb. 13, 2014 for Final Office Action dated Dec. 2, 2013 for U.S. Appl. No. 13/006,784; 24 pages.
European Response filed Mar. 3, 2014; to Official Communication dated Aug. 22, 2013; and to the Written Opinion; for European Pat. App. No. 12704944.3; 15 pages.
European Response filed Mar. 3, 2014; to Official Communication dated Aug. 22, 2013; and to the Written Opinion; for European Pat. App. No. 12701584.0; 11 pages.
PCT Search Report and Written Opinion of the ISA dated Mar. 4, 2014; for PCT Pat. App. No. PCT/US2013/059703; 12 pages.

(56) References Cited

OTHER PUBLICATIONS

Amtel Corporation; "ZigBee Pro Stack and Software Development Kit;" http://wwww.meshnetics/com/wsn-software/; 1 sheet.
Batcheldor; "Hospital Tries ZigBee to Track Patients;" RFID Journal; Jul. 21, 2006; pp. 1-2.
BelAir Networks; "Capacity of Wireless Mesh Networks;" White Paper; 2006; pp. 1-16.
Bogia; "Enabling the Future of u-Health—IEEE 11073 Personal Health Devide Standards;" Slides; Sep. 16, 2009; 38 slides.
Bowman; "Newly Ratified ZigBee Health Care Profile New Available for Public Download;" http://fiercehealthcare.com/node/40708/print; pp. 1-2.
Craig; "ZigBee Networks;" Medical Design; http://medicaldesign/com/electrical-components/zigbee_networks; Apr. 1, 2005; pp. 1-8.
Craig; "ZigBee: Wireless Control that Simply Works;" http://docs.zigbee.org/zigbee-docs/dcn/04-1427.pdf; prior to Jan. 2011; pp. 1-7.
Digi International Inc.; "ConnectPort® X4 H;" retrieved from the Internet: www.digi.com; 2008-2010; 2 sheets.
Digi International Inc.; "Demystifying 802.15.4 and ZigBee®;" White Paper; retrieved from the Internet: http://digi.com; 2008-2010; 5 sheets.
Digi International Inc.; "Xbee® & Xbee-PRO® ZB ZigBee® PRO RF modules;" http://digi.con/products/wireless/zigbee-mesh/xbee-zb-module.jsp; 1 sheet.
Digi International Inc.; "Xbee® & Xbee-Pro® ZB;" retrieved from the Internet: http://www.digi.com; 2008-2010; 2 sheets.
Dvorak; "Remote Monitoring;" http://medicaldesign.com/electrical/components/remote_monitoring/index.html; Apr. 1, 2005; pp. 1-4.
ENP Newswire; "Freescale Products Achieve ZigBee Health Care Certification;" www://allbusiness.com/health-care/health/care-facilities-nursing/14485133-1.html; May 19, 2010; 3 pages.
Huang; Medical Electronics: From Hospital and Clinic to the Home; http://www.eetimes.com/General/DisplayPrintViewContent?contentItemID=421147; Dec. 5, 2010; pp. 1-6.
ICPDAS; ZigBee Converter User's Manual, Ver 1.0; Sep. 22, 2008; pp. 1-32.
Kawai et al.; "Proposal of an Assured Corridor Mechanism for Urgent Information Transmission in Wireless Sensor Networks;" IEICE Transactions on Communications, Communications Society, Tokyo, Japan; vol. E90B, No. 10; Oct. 1, 2007; pp. 2817-2826.
Le; "Designing a Zig-Bee-Ready IEEE 802.15.4-Compliant Radio Transceiver;" www.rfdesign.com; Nov. 2004; pp. 42-50.
Miche et al.; "The Internet of Vehicles of the Second Generation of Telematic Services;" ERCIM News, ERCIM, Paris, FR; vol. 77; Apr. 2, 2009; pp. 43-45.
Norris et al.; Single-Chip ZigBee for Indoor Mobile Telemetry; Presentation; Jun. 21, 2005; pp. 1-29.
Pinto; "WMM—Wireless Mesh Monitoring;" Technical Report; 2009; pp. 1-25.
Sailhan et al., :Wireless Mesh Network Monitoring: Design, Implementation and Experiments; In Proceedings of IEEE workshop on Distributed Autonomous Network Management (DANMS); 2007; pp. 1-6.
Skibniewski et al.; "Utiquitous Computing: Object Tracking and Monitoring in Construction Processing Utilizing Zigbee™ Networks;" 23$^{rd}$ International Symposium on Automation and Robotics in Construction (ISCAR2006); Oct. 3-5, 2006; pp. 1-6.
Stewart; "ZigBee Build Reliable Zigbee-Based Solutions;" EE Times—Asia; Apr. 16-30, 2006; pp. 1-2.
Texas Instruments; Choose your ZigBee Solution with TI; 1Q 2010; 1 sheet.
Texas Instruments; Consumer Medicai Applications Guide; retrieved from the Internet: http://www.ti.com/medical.; 2010 34 pages.
Texas Instruments; "RF/IF and ZigBee® Solutions;" http//focus/ti/com/analog/docs/gencontent/tsp?familyID=367&gen-Content=ID24190&DC . . . ; Dec. 8, 2010; 2 sheets.
Texas Instruments; ZigBee® Wireless Networking Overview; 1Q 2010; 1 sheet.
The Silicon Horizon, Inc.; TechFX ZigBee Tools v1.0; 2007-2008; pp. 1-52.
Tutorial-Reports.com; "Zigbee Tutorial;" http://www.tutorial-reports.com/book/print/152; Nov. 1, 2010; pp. 1-2.
Unknown Author; "The Nokia Network Monitor;" http://www.panuworkd.net/nuukieworld/misc/netmon/index/htm; Oct. 30, 2005; pp. 1-2.
Versel; "ZigBee Alliance Ratifies Wireless Protocol for Low-Power Medical Devices;" retrieved from the Internet: http://www.fiercemobilehealthcare.com/story/zigbee-alliance-ratifies-wirelesss-protocol-lo . . . ; Apr. 6, 2010; pp. 1-2.
Wellspring; Router, Tageway, Base Station, Cell Modern Specification and Submittal; http://h2odegree.com/documents/ReferenceLibrary/OtherProductsLiterature/RouterGatewayBaseSpecSheetsSubmittal.pdf; prior to Jan. 2011; 5 pages.
Wellspring; "Wellspring Switches to a ZigBee-Cellular Hybrid System;" Press Release; Feb. 20, 2006; pp. 1-3.
ZigBee® Wireless Sensor Applications for Health, Wellness and Fitness; http://dics.zigbee.org/zigbee-docs/dcn/09-4962.pdf; Mar. 2009; pp. 1-15.
Office Action dated Sep. 5, 2013, for U.S. Appl. No. 13/006,769, 36 pages.
Office Action dated Dec. 27, 2013; for U.S. Appl. No. 13/352,575; 31 pages.
Office Action dated Jan. 7, 2014; for U.S. Appl. No. 13/353,565; 33 pages.
Office Action dated May 15, 2013; for U.S. Appl. No. 13/006,784; 35 pages.
Response filed Aug. 14, 2013; to Office Action dated May 15, 2013; for U.S. Appl. No. 13/006,784; 13 pages.
Final Office Action dated Dec. 2, 2013; for U.S. Appl. No. 13/006,784; 38 pages.
European Comments on Written Opinion dated Nov. 8, 2013; for EP Pat. App. No. 12708203.0; 2 pages.
PCT Search Report and Written Opinion of the ISA; for PCT Pat. App. No. PCT/US2012/021007; dated Sep. 20, 2012; 16 pages.
PCT International Preliminary Report on Patentability; dated Jul. 25, 2013; for PCT Pat. App. No. PCT/US2012/021007; 12 pages.
Article 19 Amendment; dated Nov. 16, 2012; for PCT Pat. App. No. PCT/US2012/021007; 7 pages.
PCT Search Report and Written Opinion of the ISA for PCT Pat. App. No. PCT/US2012/068895; dated Mar. 15, 2013; 14 pages.
PCT Search Report and Written Opinion of the ISA; dated Apr. 1, 2013; for PCT Pat. App. No. PCT/US2012/068892; 12 pages.
PCT Search Report and Written Opinion of the ISA; for PCT Pat. App. No. PCT/US2013/020069; dated Feb. 1, 2013; 16 pages.
PCT Search Report and Written Opinion of the ISA; for PCT Pat. App. No. PCT/US2013/020071; dated Feb. 1, 2013; 10 pages.
PCT Search Report and Written Opinion of the ISA; dated Apr. 1, 2013; for PCT Pat. App. No. PCT/US2012/068888; 15 pages.
PCT Search Report and Written Opinion of the ISA; dated Dec. 3, 2012; for PCT Pat. App. No. PCT/2012/025906; 19 pages.
PCT International Preliminary Report on Patentability of the ISA; dated Sep. 12, 2013; for PCT Pat. App. No. PCT/US2012/025906; 14 pages.
Article 19 Amendment; dated Feb. 4, 2013; for PCT Pat. App. No. PCT/US2012/025906; 9 pages.
PCT Search Report and Written Opinion of the ISA; dated Apr. 29, 2013; for PCT Pat. App. No. PCT/US2013/021530; 10 pages.
PCT International Preliminary Report on Patentability; dated Jul. 25, 2013; for PCT Pat. App. No. PCT/US2012/021008; 7 pages.
PCT International Search Report; dated Aug. 2, 2012; for PCT Pat. App. No. PCT/US2012/021008.
Office Action dated Nov. 16, 2012; for U.S. Appl. No. 13/037,886I 19 pages.
Response filed Feb. 14, 2013; for Office Action dated Nov. 16, 2012; for U.S. Appl. No. 13/037,886I 14 pages.
Final Office Action dated May 22, 2013; for U.S. Appl. No. 13/037,886I 15 pages.

(56) References Cited

OTHER PUBLICATIONS

Response filed Jul. 12, 2013; for Final Office Action dated May 22, 2014; 14 pages.
Notice of Allowance dated Oct. 9, 2013; for U.S. Appl. No. 13/037,886; 11 pages.
Request for Continued Examination filed Jan. 24, 2014; for U.S. Appl. No. 13/037,886; 2 pages.
Amendment filed Mar. 26, 2014, to Office Action dated Dec. 27, 2013; for U.S. Appl. No. 13/352,575; 12 pages.
Amendment filed Mar. 26, 2014; to Office Action dated Jan. 7, 2014; for U.S. Appl. No. 13/353,565; 15 pages.
Amendment and Response to Restriction Requirement for Office Action dated Feb. 10, 2014; filed Mar. 21, 2014; for U.S. Appl. No. 13/352,608; 7 pages.
Letter from CCPIT Patent and Trademark Law Office dated Mar. 3, 2014; for Chinese Pat. App. No. 201280011025.0; 1 page.
Chinese Voluntary Amendment (including English translation) received Mar. 3, 2014; for Chinese Pat. App. No. 201280011025.0; 16 pages.
Office Action dated May 27, 2014; for U.S. Appl. No. 13/334,463; 48 pages.
Mexican Notice of Allowance dated May 7, 2014; for Mexican Pat. App. No. MX/a/2013/009985; 2 pages.
Notice of Allowance dated Apr. 30, 2014; for U.S. Appl. No. 13/241,620; 21 pages.
Office Action dated Apr. 29, 2014; for U.S. Appl. No. 13/352,608; 50 pages.
Mexican Official Action received May 2, 2014, for Mexican Pat. App. No. MX/A2013/008157; 3 pages.
Mexican Office Action received Apr. 22, 2014; for Mexican Pat. App. No. MX/a/2013/008154; 4 pages.
Response to Office Action dated Apr. 29, 2014 for U.S. Appl. No. 13/352,608, filed on Jan. 18, 2012.
Notice of Allowance dated Jun. 9, 2014 for U.S. Appl. No. 13/006,769, filed on Jan. 14, 2011.

REMOTE MONITORING SYSTEMS FOR MONITORING MEDICAL DEVICES VIA WIRELESS COMMUNICATION NETWORKS

RELATED APPLICATIONS

This application is a continuation application under 35 U.S.C. 120 and claims the benefit to co-pending U.S. application Ser. No. 13/037,886 filed Mar. 1, 2011 entitled "Remote Monitoring Systems for Monitoring Medical Devices Via Wireless Communication Networks," which is incorporated by reference in its entirety herein for all purposes.

This application is related to U.S. application Ser. No. 13/006,769, filed Jan. 14, 2011, entitled "Wireless Relay Module for Remote Monitoring Systems", and to U.S. application Ser. No. 13/006,784, filed Jan. 14, 2011, entitled "Medical Device Wireless Network Architectures," each of which is incorporated by reference in its entirety herein.

FIELD OF THE INVENTION

The present application is directed to a remote monitoring system for monitoring medical devices in communication with a wireless communication network, and more particularly, to a remote monitoring system for monitoring medical devices that communicate with the wireless communication network via one or more wireless relay modules and a wireless relay network.

BACKGROUND OF THE INVENTION

In critical care and home care health service centers including hospitals, clinics, assisted living centers and the like, care giver-patient interaction time is at a premium. Moreover, response times by care givers to significant health conditions and events can be critical. Systems of centralized monitoring have been developed to better manage care giver time and patient interaction. In such systems, physiological data from each patient is transmitted to a centralized location. At this centralized location, a single or small number of technicians monitor all of this patient information to determine patient status. Information indicating a patient alarm condition will cause the technicians and/or system to communicate with local care givers to provide immediate patient attention, for example via wireless pagers and/or cell phones, and/or by making a facility-wide audio page.

Implementing such centralized monitoring systems using wireless networks may present a number of difficulties. In order to effectively monitor patient status using information provided by a variety of medical devices that may be dynamically assigned to patients in a variety of rooms and on a variety of floors in a facility, it would be desirable to establish communications between the medical devices and the centralized location by means of a local area network such as, for example, a "WiFi" network based on IEEE 802.11 standards. However, as such networks are typically already in place in facilities to support a variety of other functions (for example, physician access to electronic medical records (EMRs), facility administrative systems and other functions), it is often undesirable to secure sufficient local area network access for the purpose of providing centralized monitoring. Moreover, when a patient is located remotely from a critical care health service center (for example, at home), access to traditional local area network facilities such as a WiFi network may be unavailable or not sufficiently reliable to support critical care monitoring applications.

Clearly, for improved efficiencies in centralized monitoring of critical care and home care health service centers, it may be desirable to provide a single "off-site" centralized monitoring location for monitoring several geographically-dispersed critical care health service centers.

As an alternative to conventional WiFi or IEEE 801.11-based local area networks, ZIGBEE networks based on the IEEE 802.15.4 standard for wireless personal area networks have been used for collecting information from a variety of medical devices in accordance with IEEE 11073 Device Specializations for point-of-care medical device communication, including for example pulse oximeters, blood pressure monitors, pulse monitors, weight scales and glucose meters. See, e.g., *ZIGBEE Wireless Sensor Applications for Health, Wellness and Fitness*, the ZIGBEE Alliance, March 2009, which is incorporated by reference herein in its entirety. As compared to present IEEE 802.15.1 BLUETOOTH wireless personal area networks, for example, ZIGBEE networks provide the advantage of being dynamically configurable, for example, in "self-healing" mesh configurations, and operating with low power requirements (enabling, for example, ZIGBEE transceivers to be integrally coupled to the medical devices under battery power). However, transmission ranges between individual ZIGBEE transceivers are generally limited to no more than several hundred feet. As a consequence, such networks are suitable for on-site communications with medical devices, but unusable for centralized monitoring locations located off-site. Therefore, a hybrid system may be employed in which one or more wireless personal area networks are configured to facilitate on-site communications between medical devices and one or more wireless relay modules which are further configured to communicate with off-site centralized monitoring systems (for example, via a wireless wide-area network (WWAN) such as a mobile telephone data network, for example, based on a Global System for Mobile Communications (GSM) or Code Division Multiple Access (CDMA) cellular network or associated wireless data channels). Such a relay module and system are respectively described in the related patent applications entitled "Wireless Relay Module for Remote Monitoring Systems" (U.S. application Ser. No. 13/006,769, filed Jan. 14, 2011) and "Medical Device Wireless Network Architectures" (U.S. application Ser. No. 13/006,784, filed Jan. 11, 2011) which have been incorporated by reference within this patent application.

In accordance with applicable patient data privacy provisions of the Health Insurance Portability and Accountability Act of 1996 (HIPAA), communication of information between the monitored medical devices and the central monitoring location must be done securely, and medical device and associated patient information must be made available only to personnel accessing the centralized monitoring systems who are in possession of the appropriate access credentials. In order to be viable, the centralized monitoring system must also be capable of recognizing medical device information indicating an alert condition requiring response by on-site or other specialized personnel and reaching those on-site or specialized personnel to report the alert condition in a timely fashion.

Thus, it would be desirable to provide a remote, centralized medical information monitoring system that communicates over a wireless network of wide reach (for example, a wireless wide area network) with one or more critical care and/or home care health service centers via one or more wireless relay modules at each site, where the wireless relay modules relay communications provided by on-site medical devices over a wireless local area network or wireless personal area network. It would further be desirable for the centralized medical information monitoring system to be capable of also configuring medical devices according to associations with individual sites and patients, of logging communications from medical devices, of displaying medical device data to users of the centralized medical information monitoring system who are able to provide sufficient credentials, and of recognizing medical device alert conditions and reporting these conditions to responsible personnel in a timely fashion. In addition, it would be desirable for the centralized information monitoring system to be capable of transmitting information to the medical devices via the wireless relay modules for operating and maintaining the medical devices, including for example software upgrades and library upgrades downloaded to the medical devices.

SUMMARY OF THE INVENTION

The present invention is directed to a remote monitoring system and method for monitoring the status of a plurality of medical devices located remotely from the monitoring system at a patient care or home care facility. In accordance with one embodiment of the invention, one or more medical devices (including but not limited to including for example, respirators, enteral feeding devices, pulse oximeters, blood pressure monitors, pulse monitors, weight scales and glucose meters) are provided at a patient care or home care facility. An interface circuit is coupled to each medical device, and is configured for communicating with one of a plurality of the wireless relay modules via a wireless relay network. The wireless relay modules are further configured to communicate with the remote monitoring device over an internet-accessible wireless communication network, and preferably, a wireless wide-area network (WWAN) such as a mobile telephone data network including (for example, based on a Global System for Mobile Communications (GSM) or Code Division Multiple Access (CDMA) cellular network or associated wireless data channels). Also, for compliance for example with HIPAA regulations, communications over each of the wireless networks are preferably conducted securely.

The remote monitoring system and method includes a device integration server in communication with the wireless relay modules for receiving data packets from the wireless relay modules including information provided by the medical devices. This information includes identification of an associated medical device and data of the medical device, and is preferably encrypted or otherwise securely transmitted, for example, in compliance with HIPAA patient data privacy provisions. In addition, the information may include encrypted or otherwise securely transmitted patient identification information, which in addition may preferably be coded in its unencrypted state to avoid any reference to the patient's identity.

The remote monitoring system also includes a data management system including a secure device web server and a device control database, and an outbound web server. The data management system is configured to log information provided to the device integration server concerning the medical devices. The web server is configured to provide webpages including the data of the medical devices for display on a remote monitoring computer, subject to authentication of an associated data request originating from the monitoring computer.

The remote monitoring system may further be configured for secure communications with a patient care database node that securely stores associated patient information, and for providing additional access to the remote monitoring computer upon receiving sufficient requestor authentication for configuring medical devices to patients and for controlling the operation of the medical devices. In addition, the remote monitoring system may be configured to process alert messages received from the wireless relay modules and, in response, transmit text message information to the wireless relay modules to be relayed to one or more text messaging recipients. Alternatively, the remote monitoring system may be configured to transmit the text message directly to the one or more text messaging recipients.

BRIEF DESCRIPTION OF THE DRAWINGS

The invention will become more readily apparent from the Detailed Description of the Invention, which proceeds with reference to the drawings, in which.

DETAILED DESCRIPTION OF THE INVENTION

Reference will now be made in detail to exemplary embodiments of the invention, including the best modes contemplated by the inventors for carrying out the invention. Examples of these exemplary embodiments are illustrated in the accompanying drawings. While the invention is described in conjunction with these embodiments, it will be understood that it is not intended to limit the invention to the described embodiments. Rather, the invention is also intended to cover alternatives, modifications, and equivalents as may be included within the spirit and scope of the invention as defined by the appended claims.

In the following description, specific details are set forth in order to provide a thorough understanding of the present invention. The present invention may be practiced without some or all of these specific details. In other instances, well-known aspects have not been described in detail in order not to unnecessarily obscure the present invention.

For the purpose of illustrating the present invention, exemplary embodiments are described with reference to FIGS. 1-6.

In this specification and the appended claims, the singular forms "a," "an," and "the" include plural references unless the context clearly dictates otherwise. Unless defined otherwise, all technical and scientific terms used herein have the same meaning as commonly understood to one of ordinary skill in the art to which this invention belongs.

Figure 1:
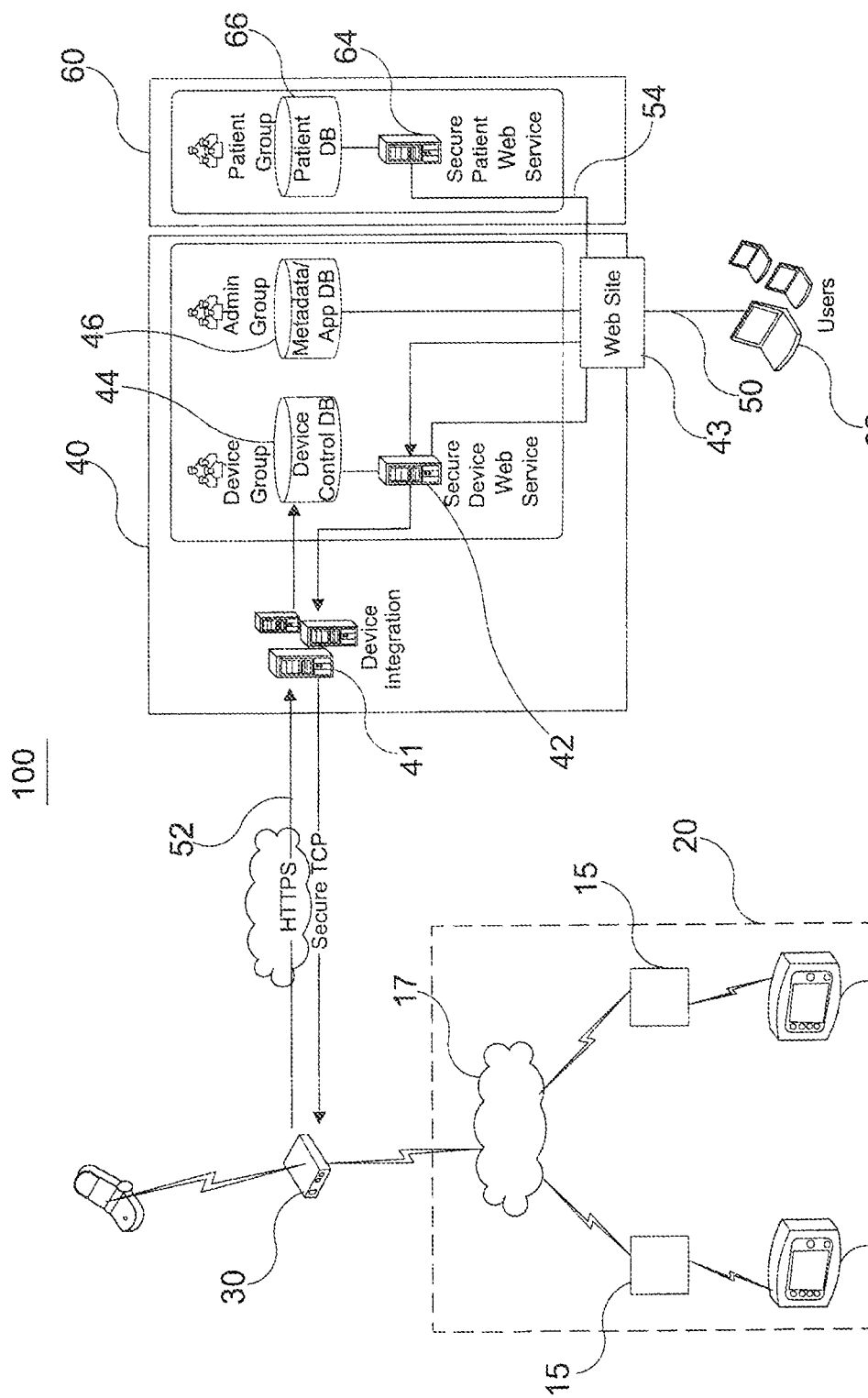
FIG. 1 presents a block diagram of an exemplary remote monitoring system for remotely monitoring medical devices according to the present invention.

A diagram of an exemplary system 100 for monitoring medical devices in accordance with the present invention is illustrated in FIG. 1. For example, one or more medical devices 10 are provided at a patient facility 20 for monitoring the medical condition and/or administering medical treatment to one or more patients. Patient facility 20 may comprise a critical care health service center (for example, including hospitals, clinics, assisted living centers and the like) servicing a number of patients, a home facility for servicing one or more patients, or a personal enclosure (for example, a backpack) that may attached to or worn by an ambulatory patient.

Associated with each medical device 10 is an interface circuit 15 that includes a transceiver having one or more of a transmitter and/or a receiver for respectively transmitting and receiving signals in a facility-oriented wireless network 17 such as, for example, a Low-Rate Wireless Personal Area Networks or "LR-WPAN," ZIGBEE network or another low-power personal area network such as a low power BLUETOOTH network, existing or presently under development or consideration. See, e.g., Houda Labiod et al., *Wi-Fi, Bluetooth, Zigbee and WiMax*, Springer 2010, which is incorporated by reference herein in its entirety. It should be understood that interface circuit 15 may be contained within or disposed external to medical device 10 in accordance with the present invention.

Also provided within the patient facility 20 are one or more relay modules 30. Each relay module 30 includes a first transceiver for receiving signals from and transmitting signals to the interface circuits 15 in the facility-oriented wireless network, and further includes a second transceiver for wirelessly transmitting signals to and receiving signals from an access point 40 via a wireless wide-area network ("WWAN") 52. Suitable WWANs for use with the present invention include, for example, networks based on a Global System for Mobile Communications (GSM) or Code Division Multiple Access (CDMA) cellular network or associated with the 2G, 3G, 3G Long Term Evolution, 4G, WiMAX cellular wireless standards of the International Telecommunication Union Radiocommunication Sector (ITU-R). See, e.g., Vijay Garg, *Wireless Communications & Networking*, Morgan Kaufmann 2007, which is incorporated by reference herein in its entirety. For compliance with HIPAA regulations, communications over each of the facility-oriented wireless network and WWAN are preferably conducted securely using, for example, using a Secure Sockets Layer (SSL) protocol or a Transport Layer Security (TLS) protocol.

As illustrated in FIG. 1, the access point 40 useable with the present invention includes an inbound server ("device integration server") 41 that incorporates or otherwise has access to a transceiver for communicating with the relay modules 30 over the WWAN. Medical device data received by the device integration server 41 over the WWAN is forwarded to a secure device web server 42, which is configured for example to log the received data in association with identification information of the associated medical devices in a device control database 44. An outbound web server 43 is configured, for example, to receive and qualify data retrieval requests submitted by one or more of remote monitoring devices 62 over a broad-band network 50 (for example, over the Internet). For each qualified request, the outbound web server 43 requests associated medical device data to be retrieved from the device control database 44 via the secure device web server 42, requests associated program data for constructing a display page from a metadata and applications database 46, and requests associated patient data to be retrieved and from a patient database 66 provided in a patient care database node 60 over a secure link 54 via a secure patient web server 64. The secure link 54 can be implemented, for example as another WWAN using a SSL protocol or a TLS protocol. By separating medical device data and patient data to be respectively stored and managed by access point 40 and patient care database node 60, certain economies of scale can be achieved by configuring the access point 40 to support a number of different patient care facilities each maintaining its own secure patient care database node 60 to ensure privacy and control of its associated patient data.

In this case, for example, a third party service provider may host the access point 40 to simultaneously support a number of distinct patient and/or home care facilities, thereby eliminating the need for each of these facilities to configure and maintain their own private access point facilities and providing hosting service to each facility that are likely far less than the costs of configuring and maintaining dedicated access point facilities by each care facility provider. It should be noted however that, consistent with principles of the present invention, access point 40 and patient care database node 60 may nevertheless be integrated into a single access point or node (for example, by a provider of a very large-scale facility provider monitoring many hundreds or thousands of patients). In either case, and as further described herein, the outbound web server 43 provides an interface for authenticated clinicians to retrieve patient and medical data from each of the patient care database node 60 and the access point 40 in a convenient and transparent manner such that the details of the configurations and operation of the access point 40 and patient care database node 60 are of no consequence to the clinicians.

Returning to FIG. 1, upon retrieving the requested medical device data and patient data, the outbound web server 43 then proceeds to format and transmit the retrieved medical device and patient data for display by one of monitoring devices 62 according to the retrieved program data.

In addition, and as will be further described herein, the device integration server 41 of FIG. 1 is configured to transmit information and commands to the relay modules 30, for example, for transmitting medical device alert messages to other WWAN-reachable nodes (for example, cellular telephones of emergency attendants), and/or transmitting operating commands and/or software or firmware updates to the medical devices 10 via the interface circuits 15 and facility-oriented wireless network 17.

Further, in addition to monitoring and sending commands to medical devices, the device integration server 41 may also be configured to receive and analyze patient metric information from the secure patient web server 64 via the outbound web server 43 and secure device web server 42, or by an alternate and direct secure data link to the secure patient web server 64 in order to prevent unsafe medical device usage based upon the patient metrics information. In this manner, the device integration server 41 would function as an additional failsafe for preventing operating errors that could result in patient harm due. For example, in the case that the patient metric information indicates that an enteral feeding pump is associated with a neonate, the device integration server 41 may act to discard remote monitoring commands programming large bolus or excessive feeding rates that could be harmful to a young child. Alternatively, if the patient metric information indicates that a specific feeding rate or bolus amount has been prescribed by a doctor or clinician, the device integration server may act to discard remote monitoring commands programming a rate or bolus that deviates from the prescription.

Figure 2:
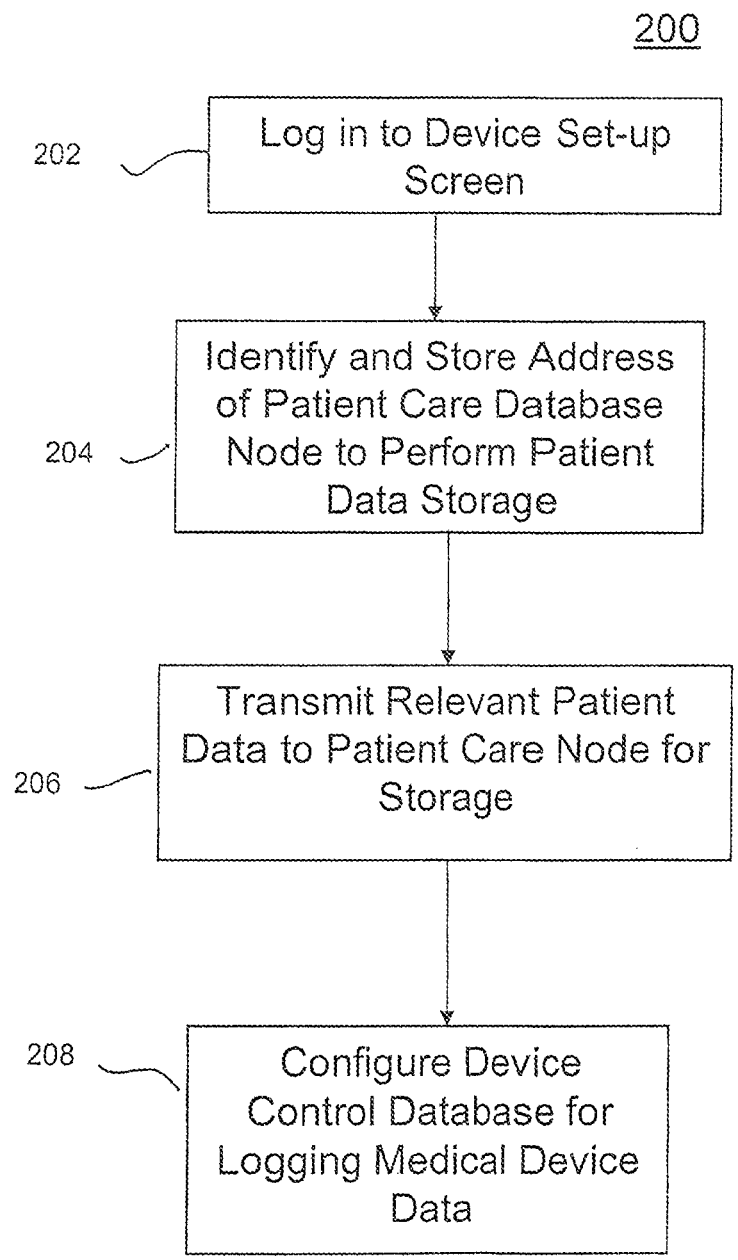
FIG. 2 presents a flow diagram illustrating an exemplary method for registering medical devices with the remote monitoring system according to FIG. 1.

FIG. 2 illustrates a flow diagram of one exemplary method 200 in accordance with the invention for registering medical devices 10 with the system 100 of FIG. 1. The method 200 begins at step 202, at which an authorized technician having access to one of the remote monitoring devices 62 provides authenticating credentials (for example, a recognized log-in and password) to the outbound web server 43, and the web server responds by transmitting a device set-up screen to the remote monitoring device 62 requesting medical device identifying information and associated patient identifying information.

At step 204, the outbound web server 43 preferably queries the metadata and application database 46 according to one or more of identifying information for the technician and/or identifying information for the patient to identify an associated patient care database node 60 from a plurality of patient care database nodes for the patient and record a destination address for the associated patient care database node 60 in the metadata and application database 46 in association with the identifying data for the medical device 10 and/or identifying information for the patient. Identifying information for the patient is preferably generated anonymously (for example as a random number), and transmitted at step 206 to the patient care database node 60 for association with securely-stored patient identifying information. At step 208 of the method 200 of FIG. 2, the outbound web server 43 requests that the secure device web server 42 assign an area of the device control database 44 for logging associated data for the medical device 10 as it is received by the device integration server 41, such that it can be later retrieved by the outbound web server 43 upon receiving an authorized request from an authenticated user operating one of the remote monitoring terminals 62.

It should be readily understood by one skilled in the art that step 204 of method 200 for identifying and storing the address of the patient care database node 60 may be omitted in accordance with the invention if a single patient care database node is utilized with system 100 of FIG. 1.

Figure 3A:
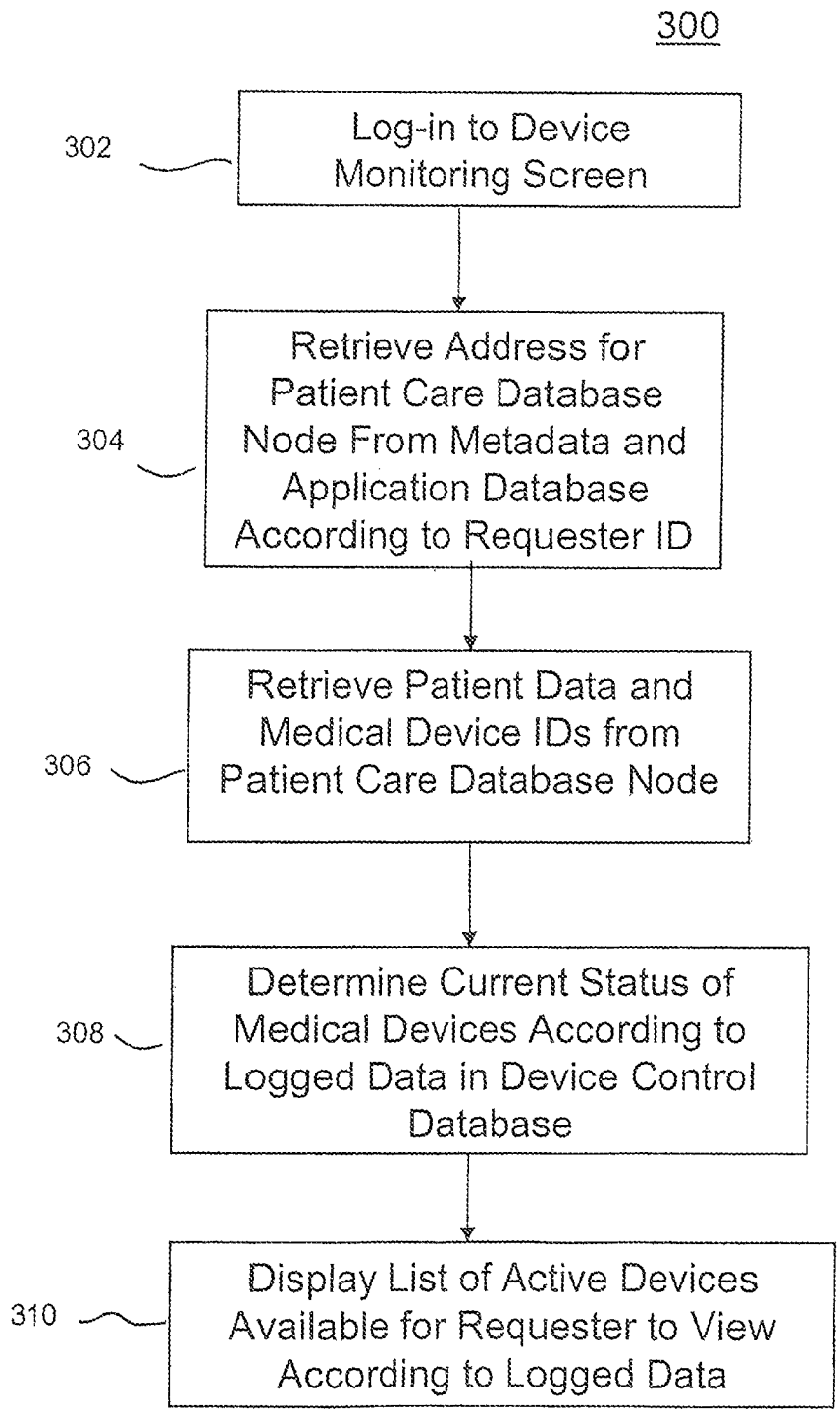
FIG. 3A presents a flow diagram illustrating an exemplary method for retrieving and viewing medical data via the remote monitoring system according to FIG. 1.

FIG. 3A presents a flow diagram illustrating one exemplary method 300 in accordance with the invention for retrieving and viewing data for a registered medical device 10 according to the system of FIG. 1. The method 300 begins at step 302 with an authorized user having access to one of the remote monitoring devices 62 provides authenticating credentials (for example, a recognized log-in and password) to the outbound web server 43. At step 304, based on the authenticating credentials, the outbound web server 43 queries the metadata and applications database 46 to identify the address of a patient care database node 60 to which the authorized user is entitled to obtain access, and at step 306, requests data from the patient care database node 60 relating to at least one identified patient for which the user is authorized to view medical device data, including for example a listing of medical devices 10 which are presently associated with the identified patient.

At step 308 of the method 300 of FIG. 3(a), the outbound web server 43 queries the device control database 44 via the secure device web server 42 for status information to determine which of the listed medical devices are presently active according to the data logged by the device control database 44. It should be noted that one or more of a medical device 10, its associated interface device 15, an associated wireless relay module 30 and/or the device integration server 41 may be programmed to provide data from the medical device 10 to the device integration server 41 at predetermined, preset intervals.

Figure 3B:
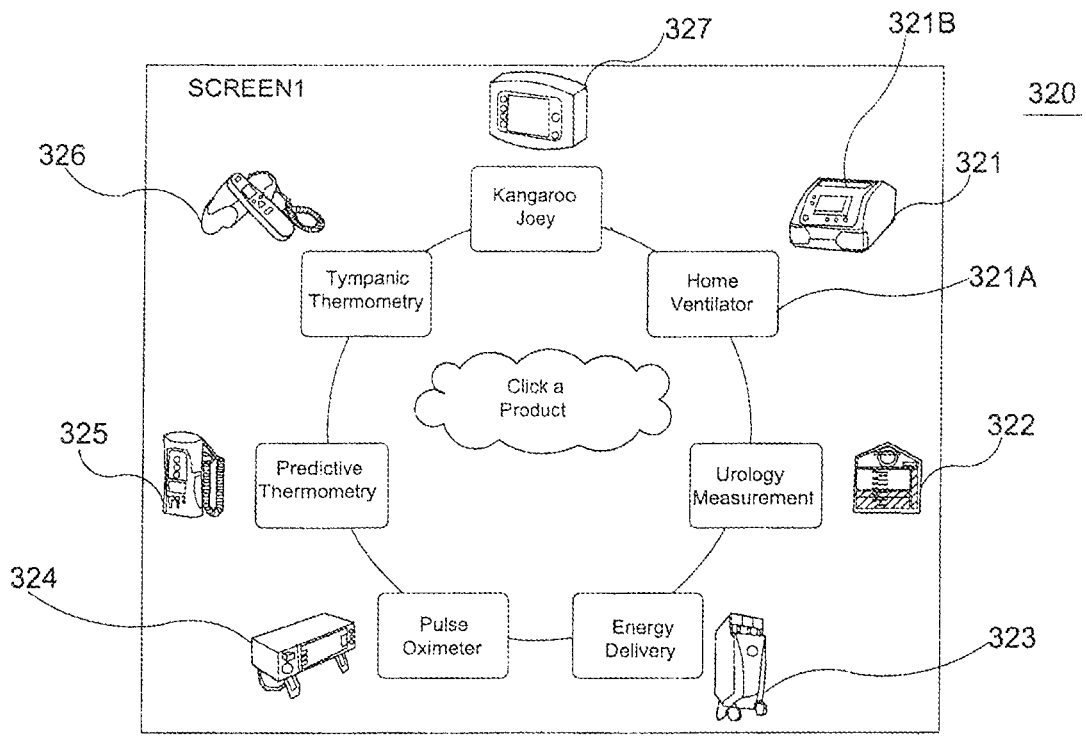
FIGS. 3B-3D illustrate exemplary screen displays for retrieving and viewing the medical data according to the method of FIG. 3A.

Upon obtaining the status information, the outbound web server 43 prepares a display page, according for example to display information retrieved from the metadata and applications database 46, to display a listing of medical devices 10 available for monitoring the user at the remote monitoring device 62. FIG. 3B presents a first exemplary screen display 320 that provides an array of medical devices 10 available for monitoring according to device type. For example, in the screen display 320 of FIG. 3B, available device types include ventilators 321, urology devices 322, energy delivery devices 323, pulse oximeters 324, predictive thermometers 325, tympanic thermometers 326 and food pumps 327. Each of the device types 321-327 in FIG. 3B is presented with an identifying label (for example, label 321A) and an identifying image (for example, image 321B) for ease of recognition.

Figure 3C:
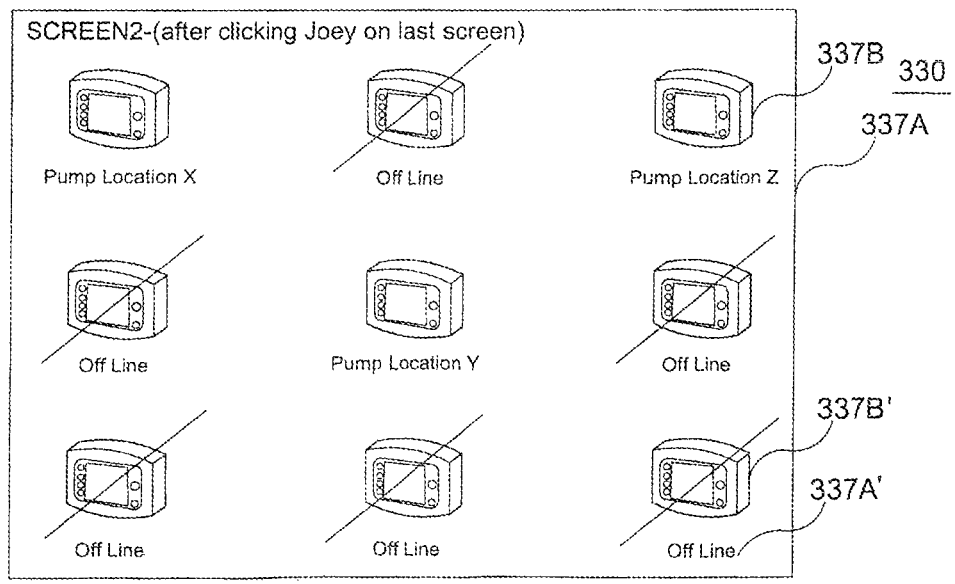

Once a device type is selected by a user (for example, in response to an associated mouse-over or mouse-click executed by the authorized user), a second exemplary screen display 330 as illustrated by FIG. 3C may preferably transmitted by the outbound web server 43 for display at the remote monitoring device 62. In the display 330, labels 337A are provided in association with images 337B in order to identify individual food pumps (for example, by patient and/or by logical or physical location). Medical devices 10 that are unavailable may for example preferably be depicted with a label 337A' ("Off Line") and an image 337B' (depicting the device with a slash or cross applied over the image) that clearly distinguish the unavailable medical devices 10 from available medical devices 10.

Figure 3D:
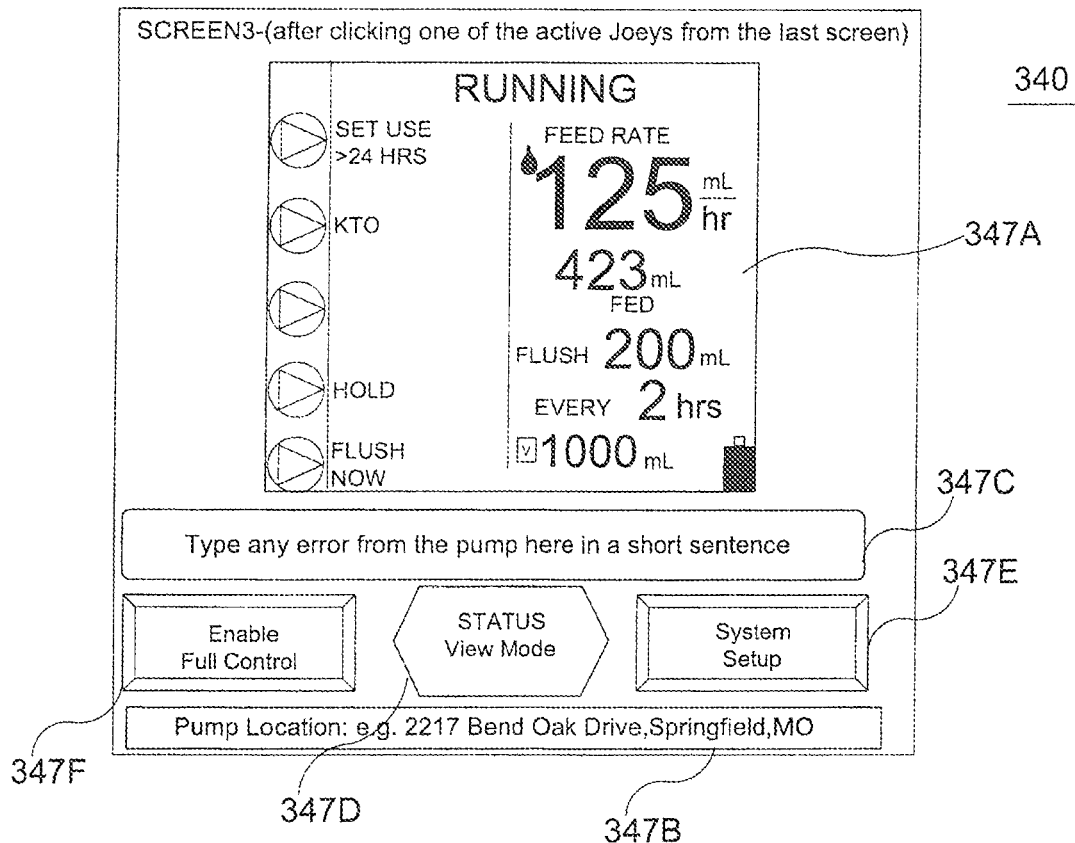

Once an individual device is selected by a user (for example, once again, in response to an associated mouse-over or mouse-click executed by the authorized user), a third exemplary screen display 340 as illustrated by FIG. 3D may preferably transmitted by the outbound web server 43 for display at the remote monitoring device 62. In the display 340, for example, device information of the medical device 10 (in this case, a food pump) is displayed in a screen 347A recreating a current screen generated by the medical device 10. In addition, the screen display 340 includes a panel 347B providing identifying information for the medical device 10 (in this case, a pump location), a panel 347C for displaying a message indicating a current error condition of the pump, and an icon button 347D for selecting an alternate "status" mode of the screen display 340. The screen display 340 also includes a control icon button 347E for selecting a system set-up screen display, and a control icon button 347F for enabling device control from the remote monitoring device 62. For example, upon selecting the control icon 347F, the screen display 340 may preferably be refreshed to include the medical devices screen 347A and one or more operable buttons that mimic the appearance of control buttons on the medical device. The control button features are described in greater detail below in relation to FIGS. 4B and 4C.

It should be readily understood that exemplary computer screen images 320, 330 and 340 and corresponding navigation depicted by FIGS. 3B, 3C and 3D are for illustration purposes only and that many other user screen images displays and interface tools may be utilized for carrying out the present invention including, for example, computer screens that depict accessible medical devices by other means than device type as illustrated in FIG. 3B. For example, as a suitable alternative to the screen image 340 of FIG. 3D that conveys information from a single medical device, it is possible to implement displays that provide information from multiple medical devices. In addition, it should be readily understood that the outbound web server 43 will preferably be operable to prepare display pages for display on any of a wide variety of display devices (including, for example, workstations, personal computers, tablet devices including tablet computers, and display-based mobile devices including personal digital assistants, smartphones, portable game systems and the like.

Figure 4A:
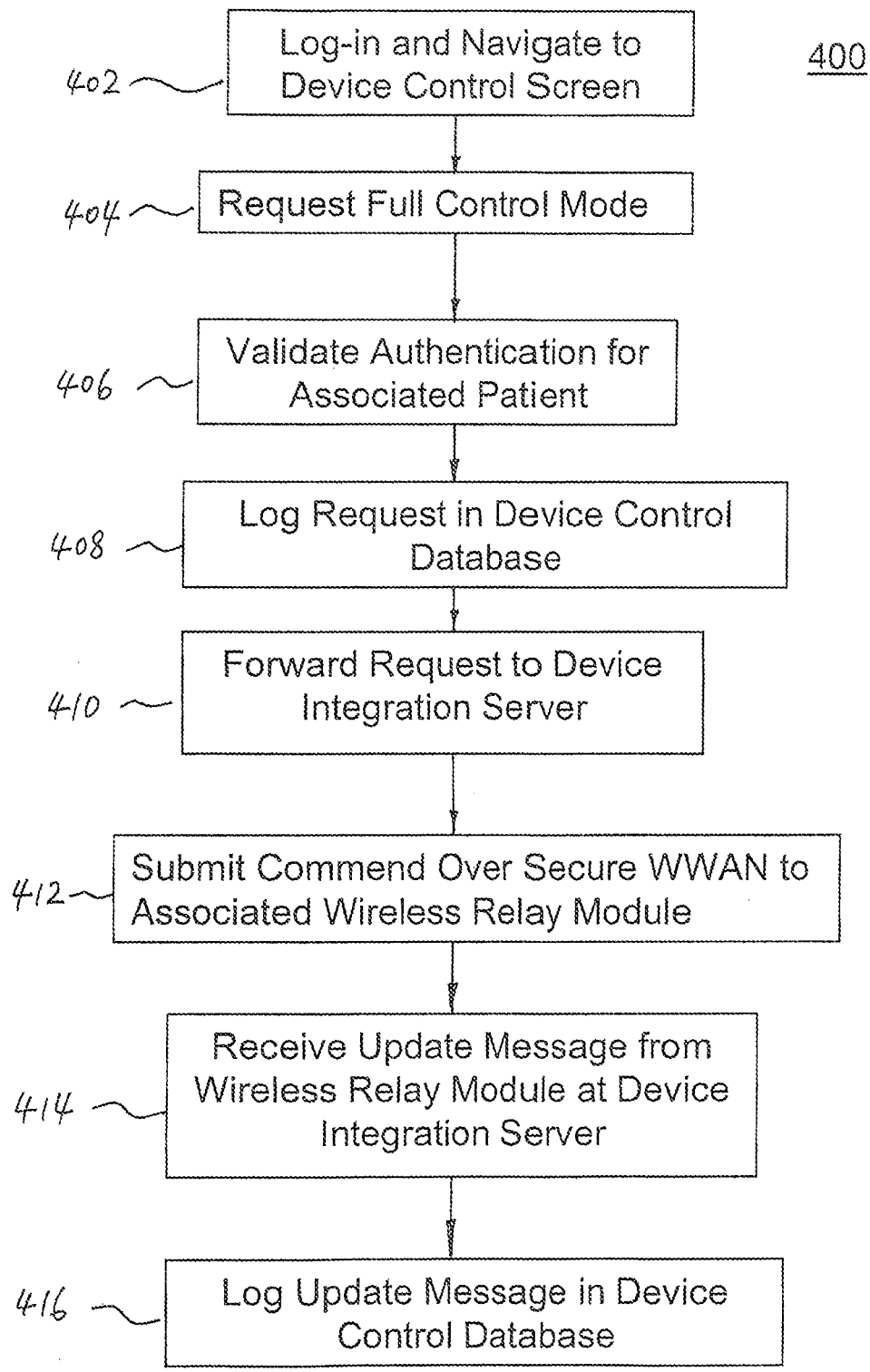
FIG. 4A presents a flow diagram illustrating an exemplary method for issuing a command to a medical device via the remote monitoring system according to FIG. 1.

FIG. 4A presents a flow diagram illustrating an exemplary method 400 in accordance with the invention for issuing a command to a medical device 10 via the system 100 according to FIG. 1. The method 400 begins at step 402 with a clinician (also referred to as a "user" herein) logging into the outbound web server 43 and navigating to the device screen display 340 of FIG. 3D (for example, as described above with reference to FIGS. 3A-3D). At step 404, the clinician proceeds to select the "Enable Full Control" button 347F of FIG. 3D to initiate an operational command directed to the medical device 10, and is preferably provided with a request for authentication pertaining in particular to the patient associated with the medical device 10. At step 406, patient authentication information provided by the clinician is forwarded by the outbound web server 43 to a patient care database node 60 according to a patient care database node address stored by the metadata and applications database 46 in association with the clinician, and the clinician is authenticated for the patient by the outbound web server 43 upon receipt of an authentication confirmed message from the patient care database node 60.

Upon receipt of the patient authentication, a control request is forwarded by the outbound web server 43 at step 408 to the secure device web server 42 to be logged in the information record of the device control database 44 that is associated with the medical device 10 (and optionally, with an anonymous ID for the patient). At step 410, the secure device web server forwards the control request to the device integration server 41, which transmits an associated device control command over the secure WWAN 52 for receipt by an associated wireless relay module 30 at step 412. The wireless relay module 30 wirelessly communicates the command to the medical device 10 via an associated device interface 15, and awaits a reply confirming execution of the command transmitted by the device interface 15.

At step 414, the device integration server 41 receives an update message from the wireless relay module 30 via the secure WWAN 52 which confirms that the command was executed by the medical device 10. At step 416, the device integration server 41 forwards the update message to the secure device web server 42 to be logged in the information record of the device control database 44 that is associated with the medical device 10. Optionally, and preferably, the secure device web server 42 forwards information pertaining to the update message to the outbound web server 43, and the outbound web server 43 prepares an updated display screen that is transmitted to the remote monitoring device 62 to indicate that the command has been executed.

Figure 4B:
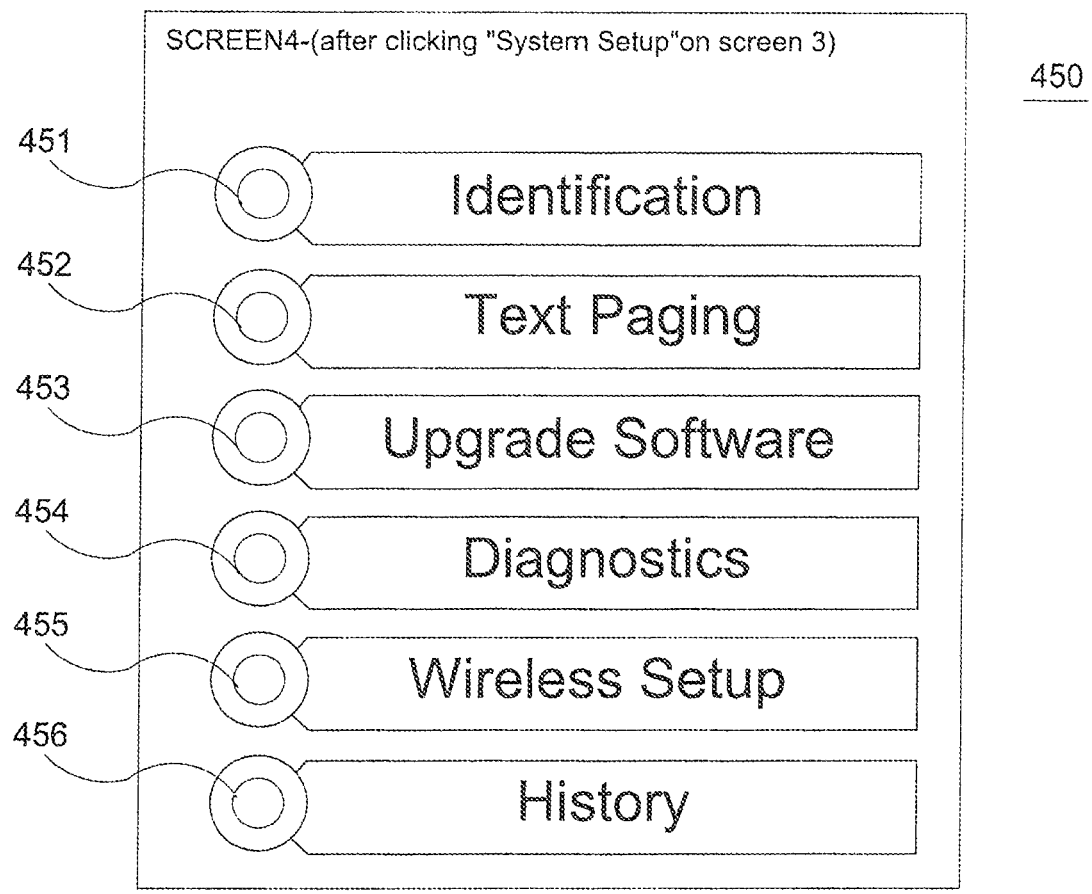
FIGS. 4B and 4C illustrate exemplary screen displays for commanding a medical device according to the method of FIG. 4A.

Alternatively, at step 404, the authenticated clinician may select the "System Setup" control icon button 347E to perform a command other than an operational command directed to the medical device 10. FIG. 4B illustrates a display screen 450 that is presented to the clinician upon selecting the control icon button 347E. The display screen 450 includes a number of icon buttons that may be selected by the clinician (for example, as the result of a mouse-over or mouse-click initiated by the clinician) to select a specific setup command. For example, icon button 451 may be selected to initiate a command for providing identification information of the medical device 10. Icon button 452 may be selected to provide text paging in response to an alert condition, as is further described herein. Icon button 453 may be selected to initiate a software or firmware download for updating the medical device 10.

Figure 4C:
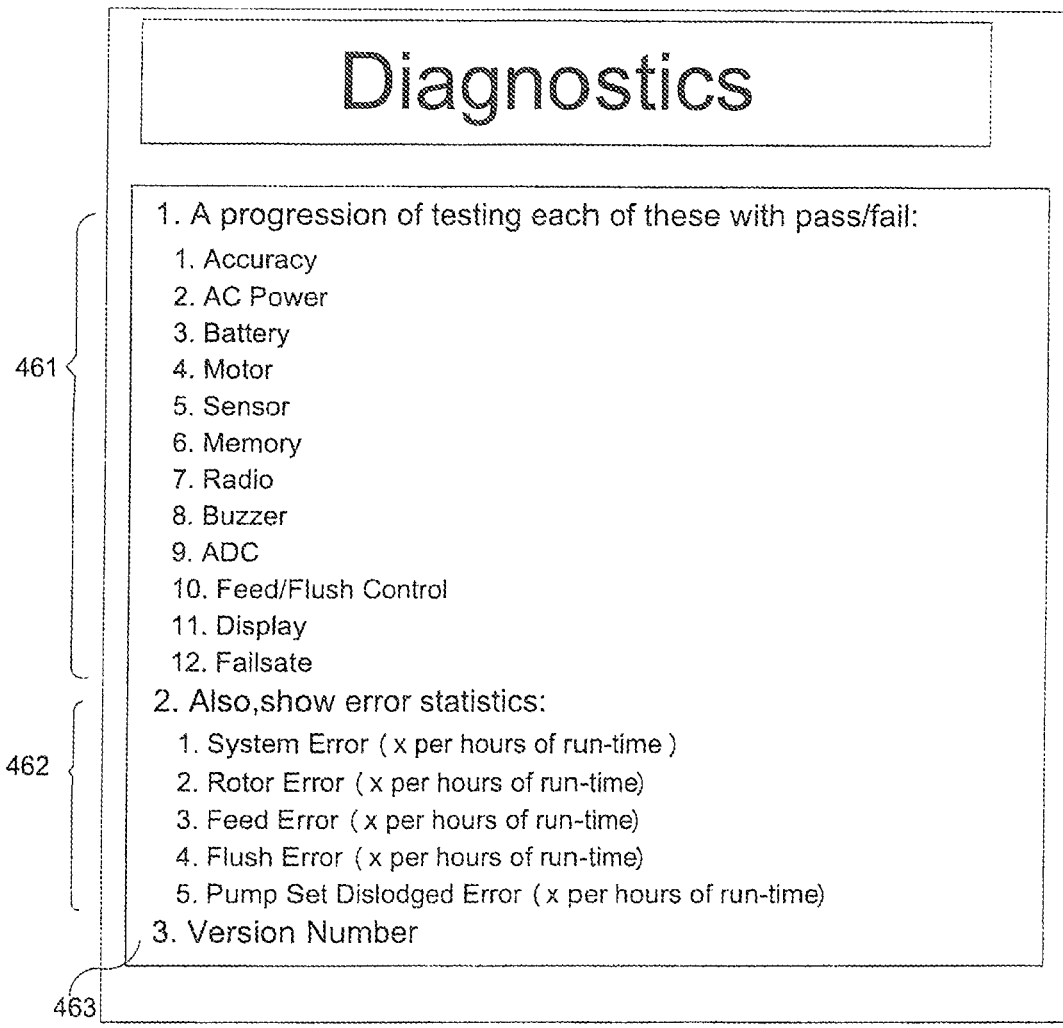

Icon button 454 may be selected to initiate a diagnostic test of the medical device 10. FIG. 4C illustrates an exemplary display screen 460 that may be displayed to the clinician upon selection of the icon button 454. Via the display screen 460 of FIG. 4C, the clinician may select one or more of (including a progression of) a series of diagnostic tests 461 directed to components of the medical device (for example, including power components, memory components, alarm components and the like). Alternatively and/or in addition, the clinician may select one or more of a series of performance statistics 462 to be gathered and displayed (for example, including various device error statistics such as feed error, rotor error and flush error rates for a food pump). In addition, perhaps most usefully before issuing a software and/or firmware download command, the clinician may select a version number test 463 to obtain version identifying information for the software and/or firmware (preferably including, for example, a software and/or firmware download history). Optionally, processes for performing the diagnostic tests 461, preparing the performance statistics 462 and identifying the software and/or firmware version number 463 may run automatically without specifically being selected by the clinician, with a complete reporting of all results on the display screen.

In a similar manner to that performed by the method of FIG. 4A, it is possible to issue a bandwidth priority command or instruction to a relay module, such as relay module 30 of FIG. 1, for the relay module to grant priority for relaying information received from a particular medical device relative to other medical devices that may send or receive communications via this relay module.

Referring again to FIG. 4B, icon button 455 may be selected to enable the clinician to specify data transfer rates, priorities and other parameters relating to the wireless transceiver of the interface device associated with the medical device. Icon button 456 may be selected to provide the clinician with the an alarm history, event history and other information as has been logged for example for the medical device in the device control database 44 of FIG. 1.

Figure 5A:
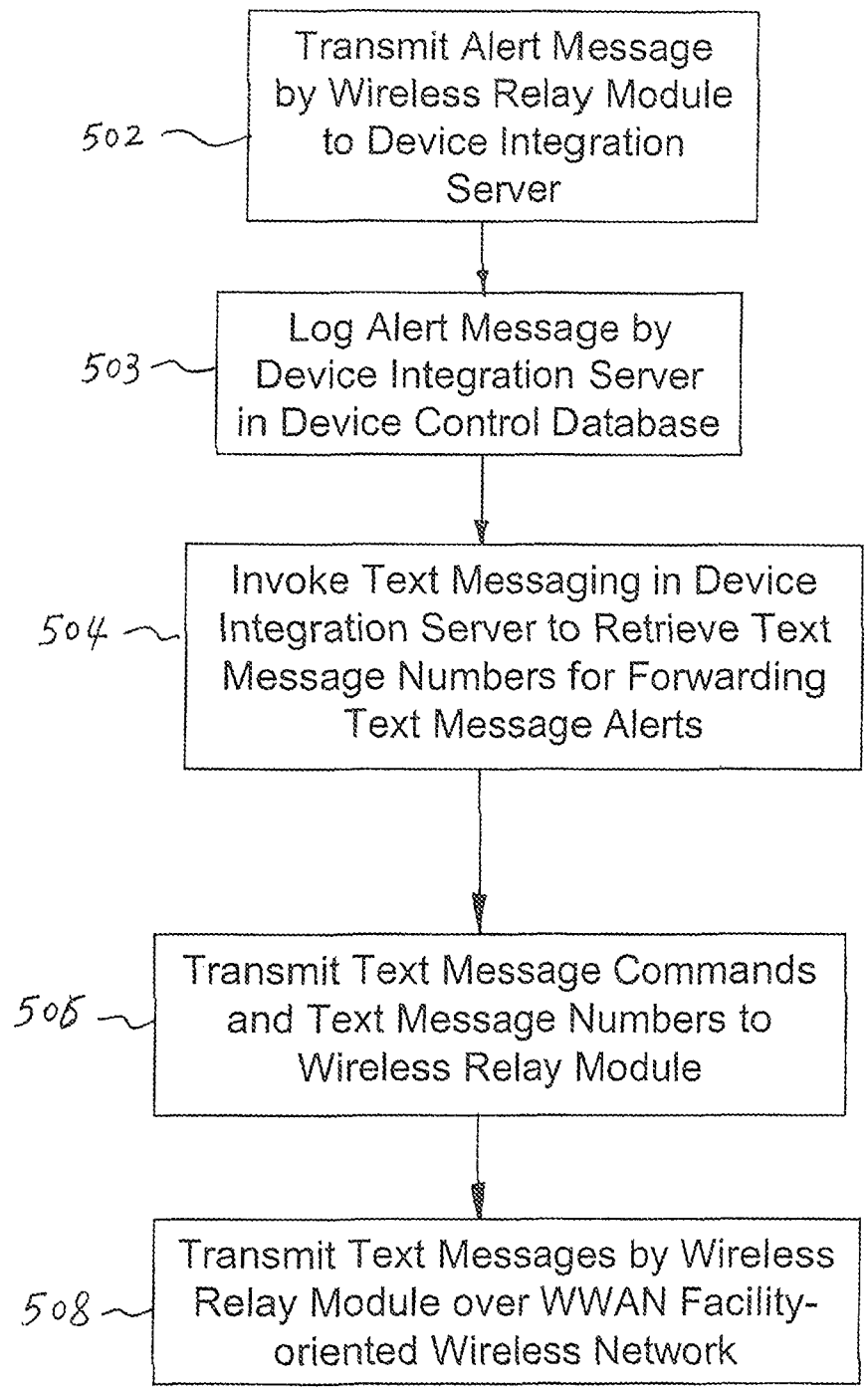
FIG. 5A presents a flow diagram illustrating an exemplary method for recognizing and reporting an alert condition according to medical data logged via the remote monitoring system according to FIG. 1.

FIG. 5A presents a flow diagram illustrating one exemplary method in accordance with the invention for recognizing and reporting an alert condition according to medical data logged via the system 100 according to FIG. 1. The method 500 begins at step 502 with the transmission of an alert message by a wireless relay module 30 over the secure WAN 52 to the device integration server 41. In this case, the wireless relay module 30 is configured to analyze a message type of a message transmitted by an associated medical device 10 to determine that the message is an alert message, and to transmit the message to the device integration server 41 upon determining that the message is an alert message (for example, as a priority message). Alternatively, the wireless relay module 30 may simply queue all messages for transmission to the device integration server 41 in order upon receipt, and rely upon the device integration server 41 to analyze an associated message type to determine that a message is an alert message.

Upon determining that the transmitted message is an alert message, the device integration server 41 proceed, at step 503, to log the message in the device control database 44, and at step 504, invokes a text messaging application that retrieves text messaging numbers associated with identifying information of the medical device 10 and/or anonymous patient identifying information. The text messaging application may preferably retrieve the text messaging numbers by queries the metadata and applications database 46 to identify the address of an associated patient care database node 60, and either making a direct request or instructing the outbound web server 43 to request the text messaging numbers from the associated patient care database node 60.

At step 506, the device integration server 41 sends one or more messages including the retrieved text messaging numbers and text message information according to the alert message to one or more wireless relay modules 30 over the secure WWAN 52. At step 508, the one or more wireless relay modules 30 transmit the text message information addressed to the text messaging numbers over one or more of the secure WWAN 52 and/or the facility-oriented wireless network 17.

Figure 5B:
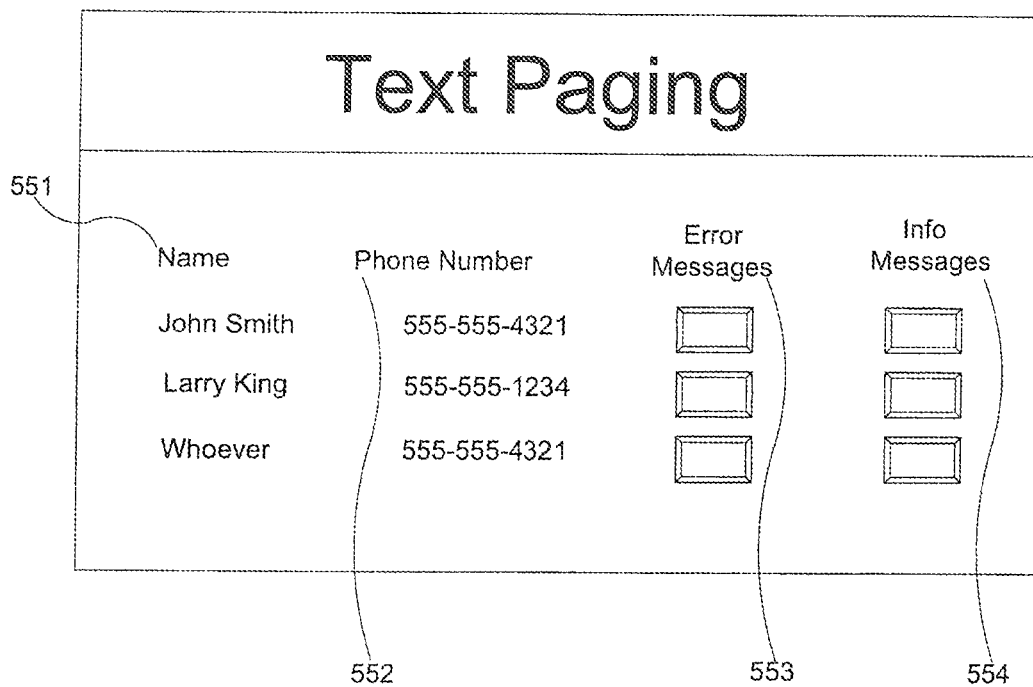
FIG. 5B illustrates ad exemplary screen display for selecting a recipient for receiving an alert message according to the method of FIG. 5A.

FIG. 5B illustrates a "Text Paging" 452 screen display 550 that may be invoked, for example, by using the method 400 of FIG. 4A for issuing a command to a medical device 10. Specifically, and with particular reference to FIGS. 3D and 4B, the text paging screen 550 is displayed at the remote monitoring device of an authenticated clinician upon the clinician's selection of the "system Setup" icon button 347e of the screen display 340, and thereafter upon the clinician's selection go the "Text Paging" icon button of the screen display 450. As illustrated in FIG. 5B, the "Text Paging" screen display 550 include a listing of one or more names 551 of individuals responsible for responding to alert messages of at least two types: "Error Messages" 553, which may for example indicate a malfunction of the medical device 10, and/or "Info Messages" 554, which may for example indicate a significant patient health condition (for example, a patient respiration rate below a preset minimum rate specified for a ventilator device 321 of FIG. 3B.

The information retrieved by the outbound web server 43 to prepare this display is preferable retrieved from the patient care database node 60, by providing on one or more of identifying information for the medical device 10 and/or anonymous patient identifying information stored in the device control database 44. Upon recognizing an alert message for the medical device 10, the information provided on the "Text Paging" screen display may be retrieved by the device integration server 41 by querying the metadata and applications server 46 to retrieve address information for the patient care database node 60, and forwarding a text paging information request to the patient care database node 60 based upon one or more of identifying information for the medical device 10 and/or anonymous patient identifying information stored in the device control database 44.

Figure 6:
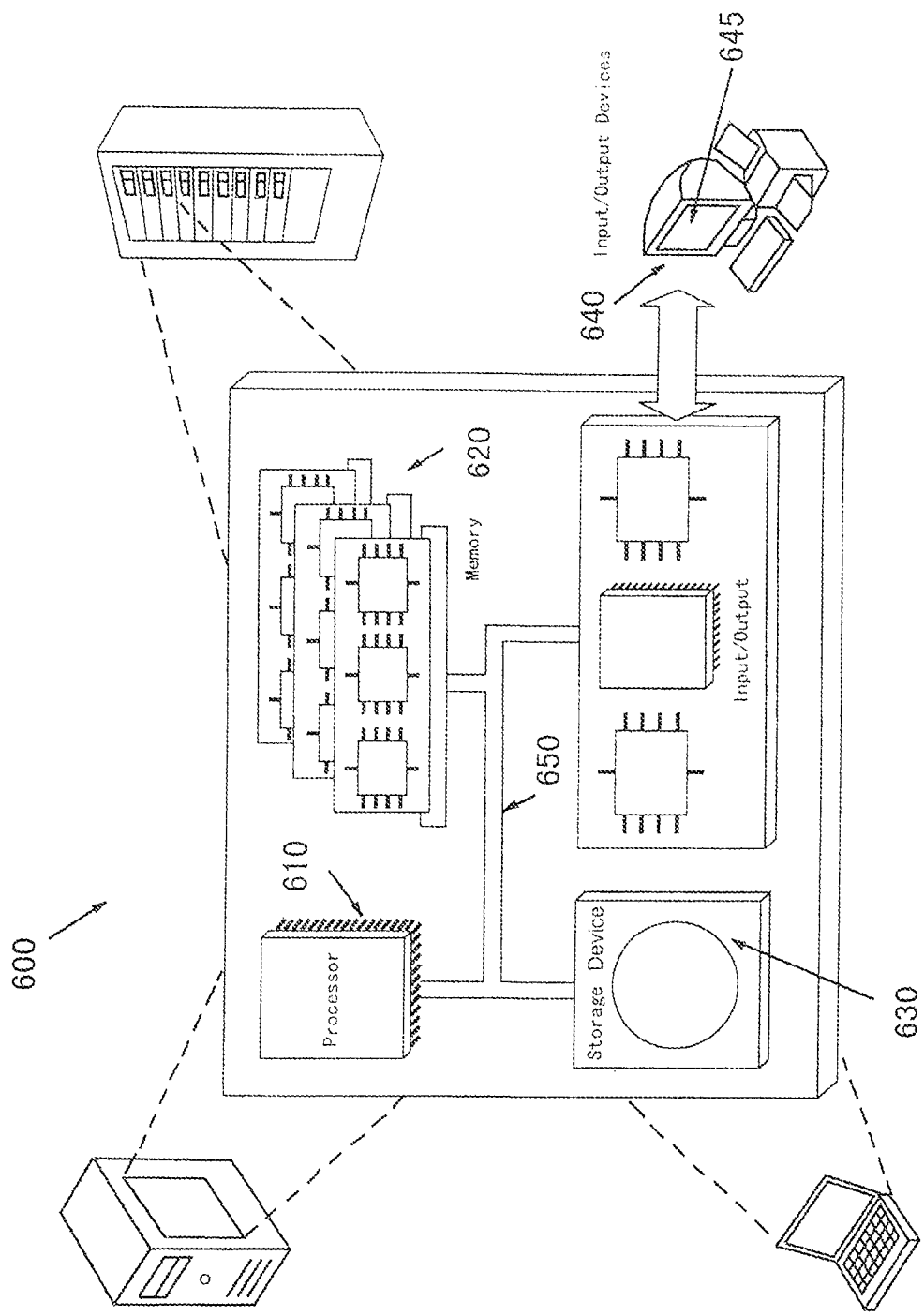
FIG. 6 presents a block diagram of an exemplary computer or server device suitable for use in the remote monitoring system according to FIG. 1.

FIG. 6 shows an illustrative computer system 600 suitable for implementing server and computer components of the present invention (for example, including device integration server 41, secure device web server 42, outbound web server 43, and secure patient web server 64). The computer system 600 as described herein may comprise, for example, a personal computer running the WINDOWS operating system, or a server computer running, WINDOWS Server, LINUX or another UNIX-based operating system. Alternatively, the computer system 600 described herein may comprise a mobile device, tablet devices or computers, or information appliance running, for example, an operating system in the group including Symbian, Android, Apple iOS, Blackberry, Microsoft Windows Phone, Linux, Palm/HP WebOS, BADA, MAEMO and MEEGO. The above-described methods carried out by the server and computer components of the present invention may be implemented on the computer system 600 as stored program control instructions directed to control application software.

Computer system 600 includes processor 610, memory 620, storage device 630 and input/output devices 640. One of the input/output devices 640 may preferably include a display 645. Some or all of the components 610, 620, 630 and 640 may be interconnected by a system bus 650. Processor 610 may be single or multi-threaded, and may have one or more cores. Processor 610 executes instructions which in the disclosed embodiments of the present invention are the steps described, for example, in one or more of FIG. 2, 3A, 4A or 5A. These instructions may be stored in one or more of memory 620 or in storage device 630. Information may be received and output using one or input/output devices 640. Memory 620 may store information and may comprise a computer-readable medium, such as volatile or non-volatile memory. Storage device 630 may provide storage for system 600 including for the example, the previously described database, and may be a computer-readable medium. In various aspects, storage device 630 may be one or more of a flash memory device, a floppy disk drive, a hard disk device, and optical disk device, and/or a tape device.

Input devices 640 may provide input/output operations for system 600. Input/output devices 640 may include one or more of a keyboard, a pointing device, and/or microphone. Input/output devices 640 may further include a display unit for displaying graphical user interfaces, a speaker and a printer and any of a number of other serial devices (for example, configured as Universal Serial Bus (USB)-based devices It should of course, be understood that while the present invention has been described with respect to disclosed embodiments, numerous variations are possible without departing from the spirit and scope of the present invention as defined in the claims.

Moreover, it is intended that the scope of the present invention include all other foreseeable equivalents to the elements and structures as described herein and with reference to the drawing figures. Accordingly, the invention is to be limited only by the scope of the claims and their equivalents.

We claim:

1. A system for enabling the remote monitoring of a plurality of medical devices, the system comprising:
   a device integrator server in communication with at least one wireless relay device, wherein said wireless relay device is configured to transmit data packets containing information provided by the medical devices, wherein each said data packet includes data identifying at least a medical device ID, a patient ID and medical device data;
   a data manager system coupled to said device integrator server, said data manager system comprising at least a device control database, and
   a web server configured for providing web pages for receiving at least the medical data and, subject to verification of the patient ID and medical device ID, transmitting the medical device data to a remote monitoring computer via a secure internet connection for displaying the medical device data by the remote monitoring computer.

2. The system of claim 1 wherein said device integrator server is configured to reply to said wireless relay when a packet type for a received data packet matches a predetermined packet type.

3. The system of claim 1 wherein said web server is further configured to perform said verification.

4. The system of claim 1 wherein said data manager system is further configured to perform said verification.

5. The system of claim 1 wherein said verification is performed by a remote system.

6. The system of claim 1 further comprising a database of addresses of at least one remotely located secure patient database, said remotely located secure patient database maintaining a patient and medical device IDs.

7. The system of claim 6 wherein said database of addresses further comprises location information associated with the respective medical device IDs, wherein said web server is configured to retrieve a destination address from said database of addresses according to said location information, retrieve patient data and medical device ID data from said remotely located patient database via said secure communications link according to said destination address, and retrieve said medical device data from said device control database according to said registered location data and said medical device ID data, said retrieved medical device data being transmitted to said web server.

8. The system of claim 1 wherein said data manager system further comprises a secure device server.

9. A system for enabling the monitoring of a plurality of medical devices, the system comprising:
   a device integrator server in communication with at least one wireless relay device via a mobile communications network, wherein said wireless relay device is configured to transmit data packets containing information provided by the medical devices, and
   said device integrator server is configured to receive the transmitted packets, to extract a packet type, a medical device ID and medical device data from each received packet, to identify a registered location associated with the extracted medical device ID, and to store the extracted medical device data with the extracted medical device ID and registered location in a device control database;
   a web server configured for hosting web pages for display on a user computer, said web server being coupled to a patient data management system via a secure communications link; and
   a data management component coupled to said device integrator server and said web server, said data management component comprising said device control database, an applications database and a secure device server, wherein
   said device integrator server is configured to reply to said wireless relay via said mobile communications network when said packet type for a received data packet matches a predetermined packet type, and
   said web server is configured to retrieve a destination address from said application database according to said registered location data, to retrieve patient data and medical device ID data from said patient data management system via said secure communications link according to said destination address, to retrieve said medical device data from said device control database via said secure device server according to said registered location data and said medical device ID data, and to prepare a web page for displaying said retrieved medical device data and patient data at the user computer.

10. A method for processing a medical device alert in a medical device monitoring system, the method comprising the steps of:
   remotely receiving a data packet from a wireless relay device in communication with a medical device;
   retrieving from the data packet a packet type, a medical device ID and a registered location of the medical device;
   determining if said packet type is indicative of an alert condition;
   retrieving alert response information from a patient data management system via a secure communications link; and
   transmitting said alert response information to said medical relay device.

11. The method of claim 10 further comprising the step of:
   storing said data packet as a data entry in a device control database, said data entry identifying said alert condition.

12. The method of claim 10, further comprising the steps of:
   retrieving said stored data entry by a web server;
   identifying a computer in communication with said web server as a current monitor for said medical device; and
   transmitting an alert by said web server for display on a web page of said computer indicating said alert condition.

13. The method of claim 10, wherein said alert response information comprises text message data for transmission by said medical relay device via a mobile communications network.

14. The method of claim 10, further comprising the step of:
   transmitting a bandwidth priority instruction to said medical relay device instructing said medical relay device to grant a service priority for relaying information between said medical device and said medical device monitoring system while said alert condition persists.

15. A method for registering a medical device for a patient with a medical device monitoring system, the method comprising the steps of:
   receiving credentials of a user of a set-up computer;
   receiving medical device identification data and associated patient identification data for a patient to be monitored;
   verifying said user is authorized to initialize a medical device associated with the medical device information;
   if verification is achieved then,
   (a) storing said medical device identification data in a device control database of said device data management system;
   (b) identifying, based on at least said received medical device identification data or patient identification data, an address for a secure patient database having information regarding said patient; and
   (c) storing said identified address in said device data management system in association with said medical device identification data; and
   forwarding said patient identification data and said address to a web server that will generate secure webpages of medical device monitor information for access by a user of a monitoring computer.

16. The method of claim 15 wherein the verifying step comprises determining whether said user is a member of a group authorized to initialize the medical device indicated in said medical device identification data.

17. A method for displaying medical device data by a medical device monitoring system, the method comprising the steps of:
   receiving credentials from a user of a monitoring computer and a request from said user for medical device information for a patient to be monitored;
   verifying said user is authorized to receive the medical device information; and
   if verification is achieved, then
   (a) identifying, based on at least said credentials and said request, an address for a secure patient database having information regarding said patient;

(b) retrieving patient data and associated medical device identification data by a web server from said patient data management system over a secure communications link;
(c) retrieving medical device data from a device control database for at least one medical device according to said retrieved medical device identification data; and
(d) transmitting said retrieved medical device data by said web server for display on said monitoring computer.

18. A method for controlling a medical device by a medical device monitoring system, the method comprising the steps of:
receiving credentials from a user of a monitoring computer and a request from said user to control a medical device;
verifying said user is authorized to control said medical device; and
if verification is achieved, then
logging said request in a device control database;
transmitting a control command based on said user request to a relay device, said relay device being configured to issue said control command to said medical device;
receiving an update message from said relay device in response to said control command; and
logging said update message in said device control database.

19. The method of claim 18, further comprising the step if said verification is achieved of:
transmitting said update message by a web server for display on said monitoring computer.

20. The method of claim 19, further comprising the step if said verification is achieved of transmitting data by said web server to said monitoring computer to display an image of a control panel of said medical device.

21. The method of claim 20, wherein said web server displays said update message by updating said image of said control panel.

22. The method of claim 21, wherein said updating includes activating an animated feature of said image.

23. The method of claim 18, wherein said verification step further comprises the steps of:
retrieving authorized use information for said medical device, and
determining that verification is achieved when said user is authorized to control said medical device and said control command is directed to an authorized use according to said authorized use information.

24. The method of claim 23, wherein said authorized use information comprises at least one of clinician instructions or prescriptions relating to a patient associated with said medical device, or patient metrics for the patient associated with said medical device.

* * * * *